(12) United States Patent
Ozaki

(10) Patent No.: US 6,876,719 B2
(45) Date of Patent: Apr. 5, 2005

(54) X-RAY CT APPARATUS

(75) Inventor: Masahiro Ozaki, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 2 days.

(21) Appl. No.: 10/674,344

(22) Filed: Oct. 1, 2003

(65) Prior Publication Data

US 2004/0114710 A1 Jun. 17, 2004

(30) Foreign Application Priority Data

Oct. 1, 2002 (JP) .................................... 2002-288247

(51) Int. Cl.[7] .............................................. G01N 23/00
(52) U.S. Cl. ................... 378/7; 378/4; 378/9
(58) Field of Search ................. 378/7, 4, 6, 9, 378/15, 19, 39

(56) References Cited

U.S. PATENT DOCUMENTS 4,114,041 A * 9/1978 Oliver ........................ 378/7
4,196,352 A * 4/1980 Berninger et al. ............. 378/7
5,068,882 A * 11/1991 Eberhard .................... 378/4
6,661,867 B2 * 12/2003 Mario et al. ................ 378/57

FOREIGN PATENT DOCUMENTS

JP 2002-172112 6/2002

* cited by examiner

Primary Examiner—Craig E. Church
Assistant Examiner—Irakli Kiknadze
(74) Attorney, Agent, or Firm—Oblon, Spivak, McClelland, Maier & Neustadt, P.C.

(57) ABSTRACT

An X-ray CT apparatus includes a plurality of X-ray irradiation sources and a plurality of X-ray detection units. Timing of irradiation of X-ray is shifted by each X-ray irradiation source, the detection unit separately obtains projection data and scatter correction data. In a scatter correction unit, scatter correction is performed based on the projection data and the scatter correction data.

21 Claims, 9 Drawing Sheets

X-RAY CT APPARATUS

CROSS-REFERENCE TO RELATED APPLICATIONS

This application is based upon and claims the benefit of priority from prior Japanese Patent Application No. P2002-288247 filed on Oct. 1, 2002, the entire contents of which are incorporated herein by reference.

BACKGROUND OF THE INVENTION

1. Field of the Invention

The present invention relates to an X-ray CT apparatus that includes a plurality of X-ray irradiation sources.

2. Description of the Related Art

In an X-ray CT apparatus, an X-ray detector detects a quantity of penetration X-ray irradiated from an X-ray tube, and collects view data based on the X-ray. A tomographic image of a patient is reconstructed based on the collected view data. The view data is a unit of data used for the reconstruction.

In a so-called 3rd generation X-ray CT apparatus, when the X-ray tube and the X-ray detector that is positioned opposite the X-ray tube are rotated around the patient 360 degrees, a limited fan-shaped X-ray is irradiated from the X-ray tube to the patient. The detector that has a plurality of detection elements arranged in an arc shape detects the X-ray penetrated through the patient. At one angle to the patient, a group of the X-ray data detected by the plurality of detection elements is called a view. It is called a scan to collect view data of a plurality of views while the X-ray tube and the X-ray detector are rotated around the patient. Furthermore, the collection cycle of the view data repeated in the scan is called a view cycle. The tomographic image is obtained by applying reconstruction process to the view data of the plurality of views with a high speed reconstruction unit, etc.

For example, when the view data of one view is collected by one degree, the view data of 360 degrees is collected by one scan, which means the number of the view cycles is 360. The image is reconstructed based on the view data of 360 views. The quality of the image improves by increasing the number of the views in the scan.

In a recent X-ray CT apparatus, the view data of 900 views is collected by one scan, for example. That is, the view data of one view is collected every 0.4 degrees, and the view data of 360 degrees is collected. In order to improve the quality of the image, the X-ray CT apparatus which collects the view data of 1200 views or 1800 views by one scan has been proposed. The view cycle is, for example, 0.3 degrees when the view data of 1200 views is collected, and the view cycle is 0.2 degrees when the view data of 1800 views is collected.

Recently, a scan time in which the X-ray tube and the X-ray detector rotate around the patient is 0.5 seconds. There is a desire to shorten the scan time to less than 0.5 seconds in order to observe a moving internal organ, such as a heart, in more detail. However, since much centrifugal force is applied to rotation portions, such as the X-ray tube and the X-ray detector when a rotation speed is fast, it is technically difficult merely to increase a rotation speed in order to shorten the scan time. One proposed solution to collect the view data of the predetermined views for a short time without increasing the rotation speed is set forth in Japanese Patent Publication (Kokai) No. 2002-172112 (the contents of which are herein incorporated by reference), which describes a high speed X-ray CT apparatus that includes a plurality of X-ray tubes and X-ray detectors (see, for example, pages 3–6 and FIG. 1).

However, new problems result from the technique proposed in 2002-172112, such as a large influence of scattered X-rays and shading occurs when the plurality of the X-ray tubes and X-ray detectors are used. The influence of the scattered X-ray is explained with reference to FIG. 1 and FIG. 2.

Figure 1:
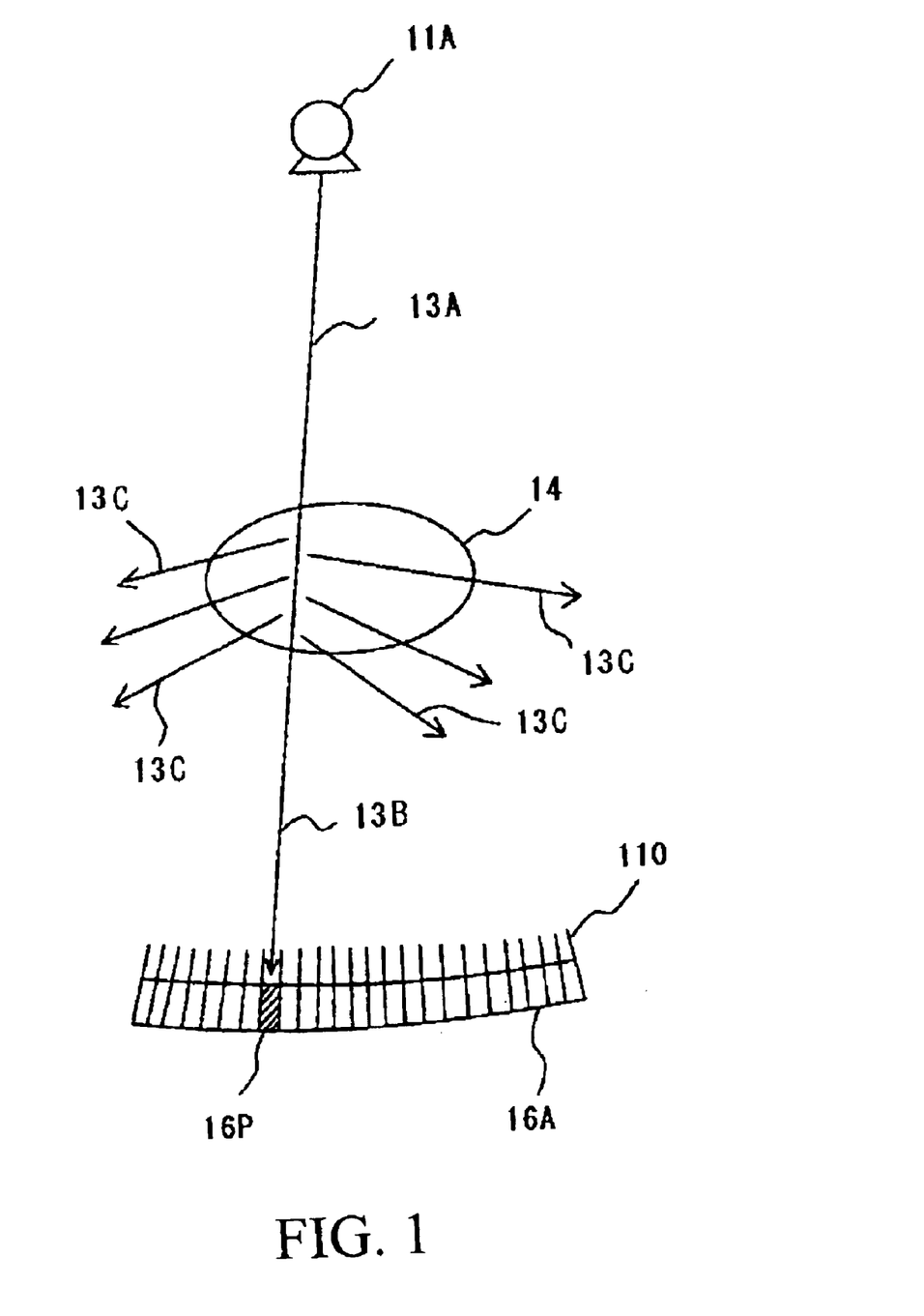
FIG. 1 shows an X-ray CT apparatus for explaining generation of scattered X-ray.

FIG. 1 shows an X-ray CT apparatus where an X-ray tube 11A is positioned opposite an X-ray detector 16A, and a patient 14 is positioned therebetween. The X-ray detector 16A includes 800 channel detection elements arranged in a line according to the spread of an X-ray path irradiated from the X-ray tube 11A. Regarding one X-ray 13A irradiated from the X-ray tube 11A to the patient 14, a part of the X-ray 13A is absorbed in the patient, and another part of the X-ray 13A penetrated through the patient 14, indicated as X-ray 13B, incidents to a channel 16P of the X-ray detector 16A along an irradiation direction. Slight remaining X-ray 13A scatters all around. A collimator 110 is positioned in front of the X-ray detector 16A according to each channel to prevent the scattered X-ray 13C from being incident to other channels.

Figure 2:
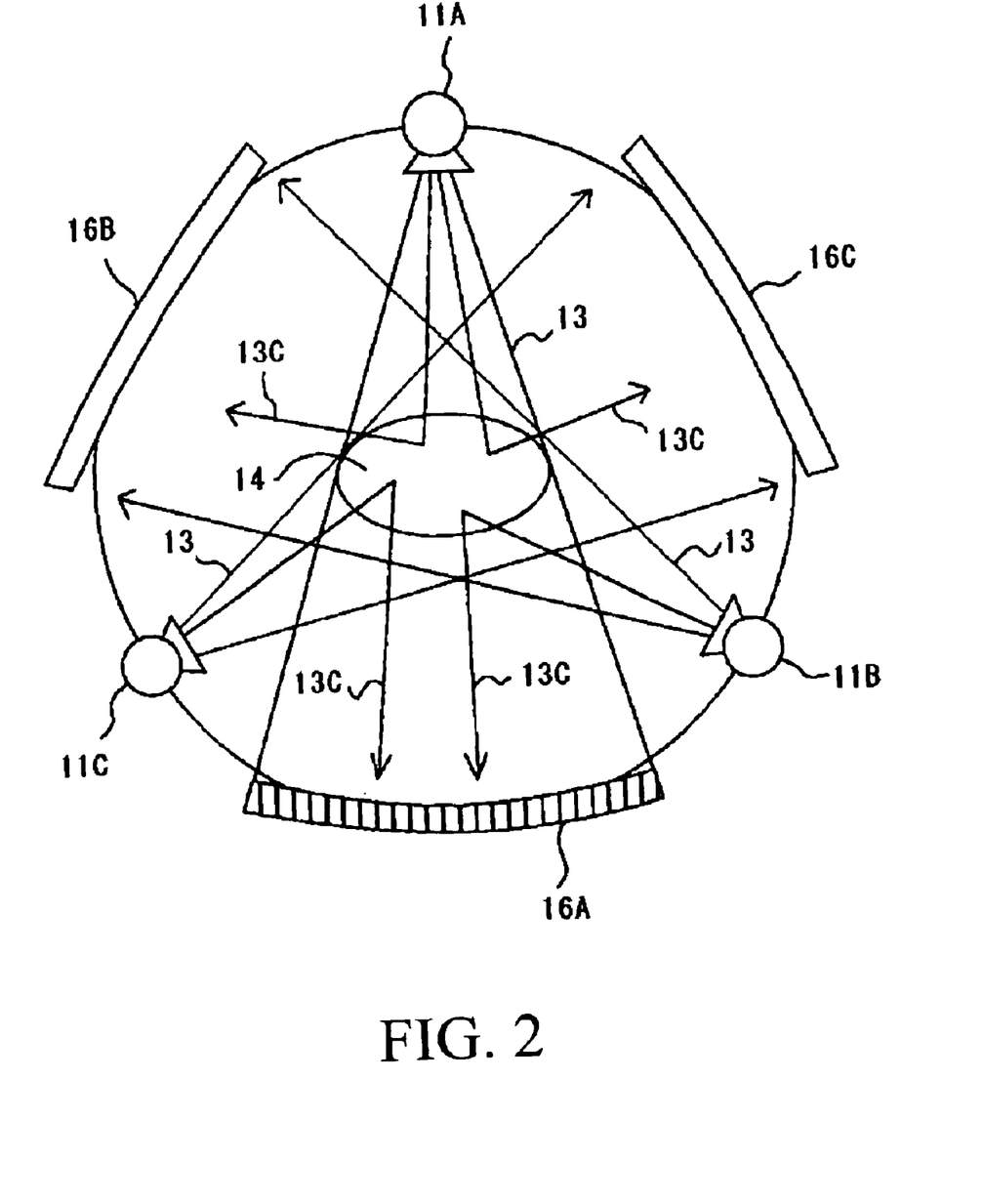
FIG. 2 shows an high speed X-ray CT apparatus for explaining generation of scattered X-ray.

However, even with the above-described configuration, the influence of the scattered X-ray is still large. FIG. 2 shows an X-ray CT apparatus where three X-ray tubes 11A, 11B, and 11C are positioned at 120 degree intervals, opposite three X-ray detectors 16A, 16B, and 16C. Each X-ray tube 11A, 11B, and 11C makes a fan-shaped X-ray path 13. In this case, the X-ray detector 16A detects the X-ray irradiated from the X-ray tube 11A, the X-ray detector 16B detects the X-ray irradiated from the X-ray tube 11B, and the X-ray detector 16C detects the X-ray irradiated from the X-ray tube 11C, respectively.

However, the X-ray detector 16A can detect the scattered X-ray 13C irradiated from the X-ray tube 11B and 11C. That is, although the incidence of the scattered X-ray irradiated from the X-ray tube 11A to the X-ray detector 16A can be reduced by the collimator as described with regard to FIG. 1, it is difficult to avoid the scattered X-ray irradiated from the X-ray tubes 11B and 11C to interfere with the X-ray detector 16A. The same is true for the other X-ray detectors 16B and 16C. For this reason, the quality of the image is deteriorated.

SUMMARY OF THE INVENTION

One object of the present invention is to ameliorate the above-mentioned problems. To that end, according to one aspect of the present invention, there is provided an X-ray CT apparatus, including: a plurality of X-ray irradiation sources, configured to rotate around an object and to irradiate X-rays to the object; a plurality of X-ray detection units, each of which is positioned opposite each of the plurality of X-ray irradiation sources and configured to detect at least one X-ray penetrated through the object, thereby obtaining projection data and scatter correction data; a control unit configured to divide a view cycle into a plurality of sub cycles, to allocate the plurality of sub cycles between obtaining the projection data and the scatter correction data, and to obtain view data by the view cycle based on the projection data and the scatter correction data; and a reconstruction unit configured to reconstruct an image of the object based on the view data.

Additionally, an X-ray CT apparatus is provided that includes: a plurality of X-ray irradiation sources, configured to rotate around an object and to irradiate X-rays to the object; a plurality of X-ray detection units, each of which is positioned opposite each of the plurality of X-ray irradiation sources and configured to detect at least one X-ray penetrated through the object; and a control unit configured to control the plurality of X-ray irradiation sources and the plurality of X-ray detection units such that at least one of the plurality of X-ray detection units obtains projection data when at least another of the plurality of X-ray detection units obtains scatter correction data.

Another X-ray CT apparatus according to the present invention includes: a plurality of X-ray tubes, configured to rotate around an object and to irradiate X-rays to the object; a plurality of X-ray detection units, each of which is positioned opposite to each of the plurality of X-ray tubes and is configured to detect at least one X-ray penetrated through the object; and a control unit configured to control the plurality of X-ray tubes and the plurality of X-ray detection units such that at least one of the plurality of X-ray detection units obtains projection data when at least another of the plurality of X-ray detection units obtains scatter correction data.

As yet another example, an X-ray CT apparatus is provided that includes: a plurality of X-ray irradiation sources configured to rotate around an object and to irradiate X-rays to the object; a plurality of X-ray detection units, each of which is positioned opposite to each of the plurality of X-ray irradiation sources and is configured to detect at least one X-ray penetrated through the object to obtain projection data and scatter correction data; a control unit configured to obtain view data by a view cycle, based on the projection data and the scatter correction data; and a reconstruction unit configured to reconstruct an image of the object based on the view data.

Alternatively an X-ray CT apparatus may include: a plurality of irradiating means, rotating around an object, for irradiating X-rays to the object; a plurality of detecting means, each of which is positioned opposite to the plurality of irradiating means, for detecting at least one X-ray penetrated through the object to obtain projection data and scatter correction data; means for dividing a view cycle into a plurality of sub cycles, for allocating the sub cycle between obtaining the projection data and the scatter correction data, and for obtaining view data by the view cycle, based on the projection data and the scatter correction data; and means for reconstructing an image of the object based on the view data.

A method for correcting scattered X-ray is also provided, including; stopping an X-ray from a first X-ray irradiation source to an object; irradiating an X-ray from a second X-ray irradiation source to the object; collecting scatter correction data of the object by a first X-ray detection unit positioned opposite to the first irradiation source when the X-ray from the first X-ray irradiation source stops and the X-ray from the second irradiation source is irradiated; irradiating the X-ray from the first X-ray irradiation source to the object; collecting projection data of the object when the X-ray from the first X-ray irradiation source is irradiated; and correcting the projection data based on the scatter correction data.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. In the drawings.

DETAILED DESCRIPTION OF THE PREFERRED EMBODIMENTS

Figure 3:
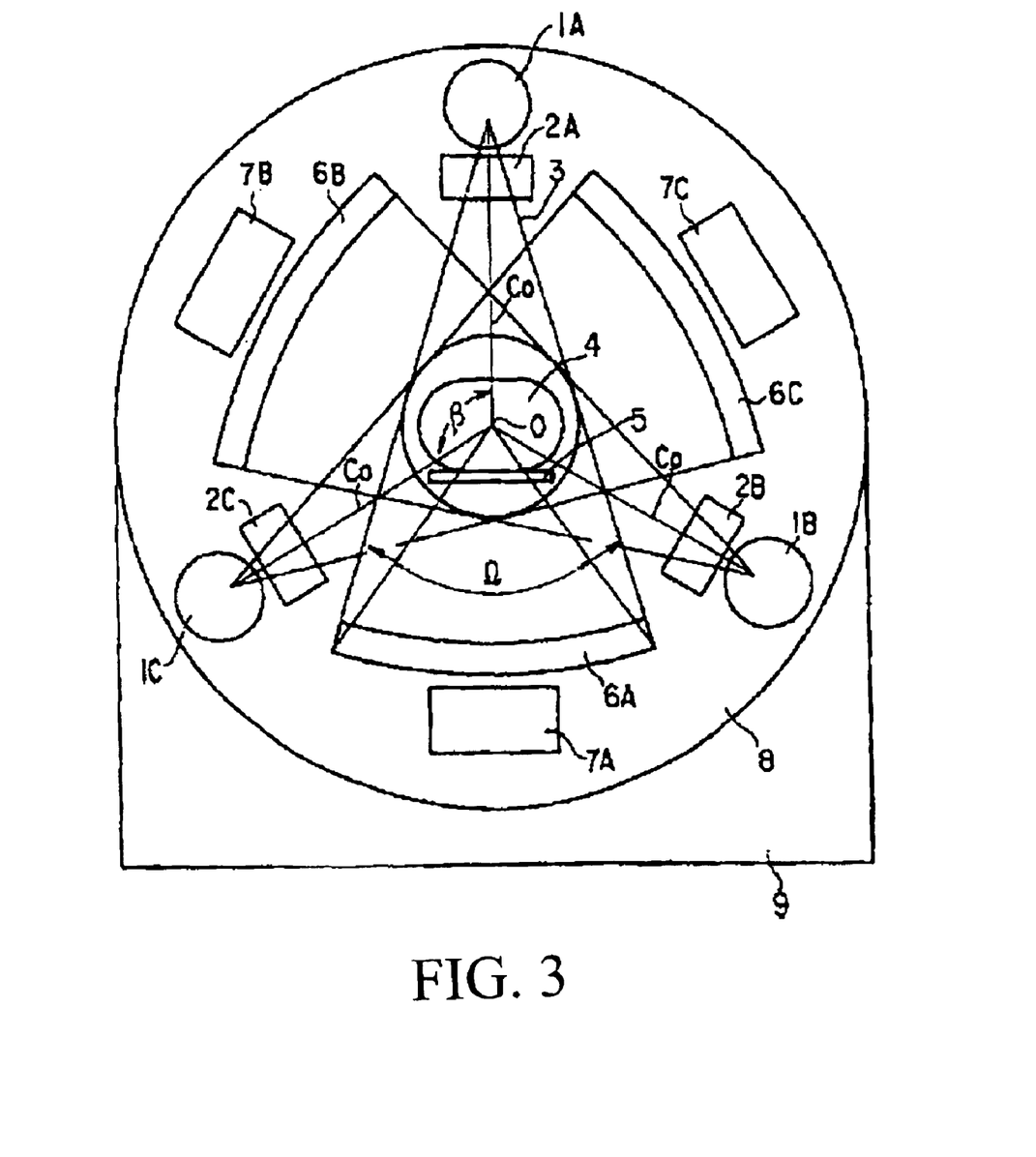
FIG. 3 is a block diagram of a gantry of an X-ray CT apparatus in a non-limiting first embodiment.

A first embodiment of an X-ray CT apparatus is explained with reference to FIG. 3 through FIG. 7. The X-ray CT apparatus includes three X-ray tubes 1A, 1B, and 1C as shown in FIG. 3. The X-ray tubes 1A, 1B, and 1C are arranged at equal intervals on a concentric circle which has a rotation center O. An angle $\beta$ between center lines Co, each of which travels through each X-ray tube and the rotation center O, is approximately 120 degrees. That is, when the X-ray tube 1A is positioned at 0 degrees, the X-ray tube 1B is positioned at 120 degrees and the X-ray tube 1C is positioned at 240 degrees.

Slits 2A, 2B and 2C are placed at X-ray irradiation window of the X-ray tubes 1A, 1B and 1C, respectively. The slits 2A, 2B, and 2C make fan-shaped X-ray paths 3 that are collimated and have a predetermined thickness. The center line Co is also a center line of the X-ray path 3. A plate on which a patient 4 is situated is positioned such that the patient 4 is on the rotation center O. The X-ray CT apparatus further includes three X-ray detectors 6A, 6B, and 6C corresponding to the X-ray tubes 1A, 1B, and 1C, and also includes three data acquisition units 7A, 7B, and 7C corresponding to the X-ray detectors 6A, 6B, and 6C.

A combination of the X-ray tube 1A and the X-ray detector 6A is referred to as "combination A," that of X-ray detector 1B and the X-ray detector 6B is referred to as "combination B," and that of X-ray detector 1C and the X-ray detector 6C is referred to as "combination C." The X-ray irradiated from the X-ray tube 1A and penetrated through the patient 4 is detected by the X-ray detector 6A and is collected by the data acquisition unit 7A as projection data. Regarding the other X-rays irradiated from the X-ray tubes 1B and 1C, these X-rays are collected by other acquisition units 7B and 7C as well.

By way of non-limiting example, the X-ray tubes 1A, 1B, and 1C, the slits 2A, 2B, and 2C, the X-ray detectors 6A, 6B, and 6C, and the data acquisition units 7A, 7B, and 7C are fixed in a rotating gantry 8. The rotating gantry 8 is rotated by a rotation mechanism at the rotation center O, and is supported by a fixed gantry 9. The angle $\Omega$ represents the fan angle degrees.

Figure 4:
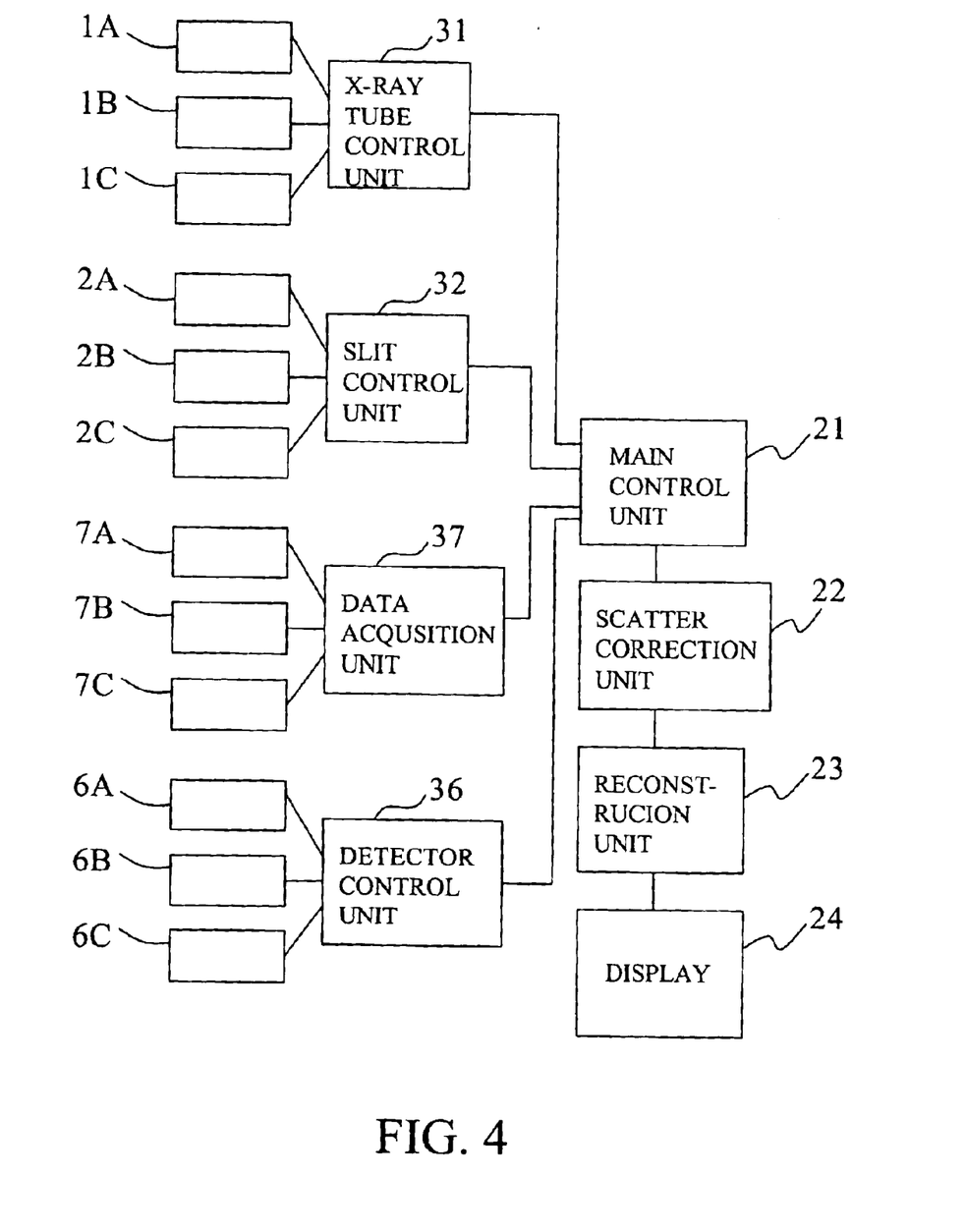
FIG. 4 is a block diagram of the X-ray CT apparatus in the first embodiment.

As shown in FIG. 4, the X-ray CT apparatus includes a control unit body that is connected to the rotating gantry 8 via the fixed gantry 9. The control unit body includes an X-ray tube control unit 31, a slit control unit 32, a detector control unit 36 and a data acquisition control unit 37 that control the X-ray tubes 1A through 1C, the slits 2A through 2C, the X-ray detectors 6A through 6C, and the data acquisition units 7A through 7C, respectively. Further, the control unit body includes a main control unit 21 that controls the X-ray tube control unit 31, the slit control unit 32, the detector control unit 36 and the data acquisition control unit 37. Furthermore, the control unit body includes a scatter correction unit 22 that corrects a scattered X-ray, a reconstruction unit 23 that reconstructs an image, and a display 24 that displays the reconstructed image.

An operation of the X-ray CT apparatus now follows. The projection data is collected under control of the main control unit 21, rotating the rotating gantry 8. When the X-ray tube 1A rotates from the position of 0 degree to the position of 120 degrees and the projection data is collected, the X-ray tube 1B rotates from the position of 120 degrees to the position of 240 degrees to collect the projection data. Similarly, the X-ray tube 1C rotates from the position of 240 degrees to the position of 360 degrees to collect the projection data. That is, the projection data of 360 degrees is collected while the rotating gantry 8 rotates 120 degrees. Therefore, compared with the X-ray CT apparatus including only one X-ray tube and one X-ray detector, the scan time can be theoretically shortened to ⅓, without increasing the rotation speed.

Figure 5:
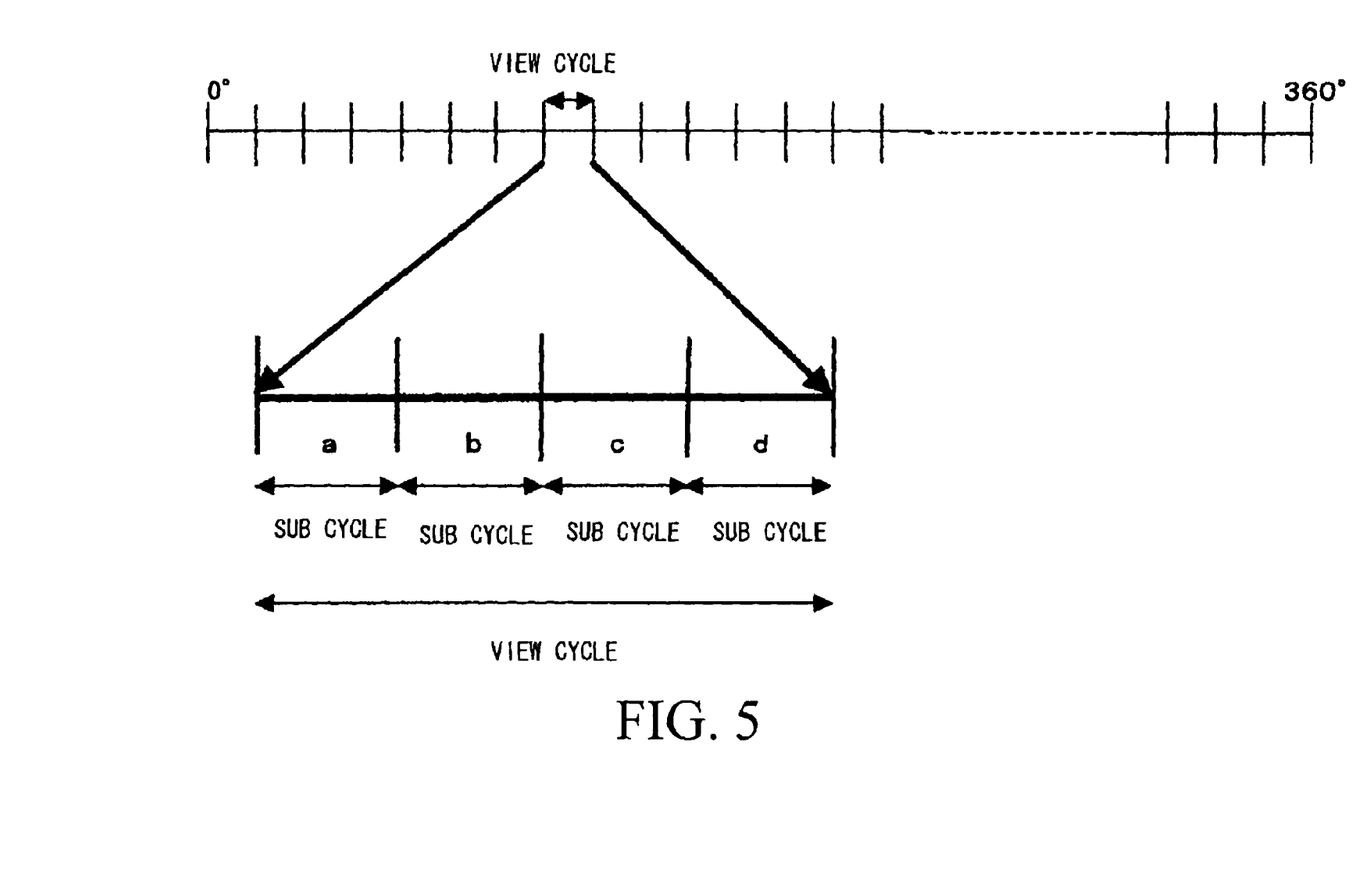
FIG. 5 is an illustration for explaining one example of data collection timing by the X-ray CT apparatus in the first embodiment.

Detection of the X-ray by the X-ray detector will now be explained in detail. The projection data of the patient and the scatter correction data for correcting the scattered X-ray in the projection data are separately collected. The view cycle is divided into a plurality of sub cycles. In the first embodiment, the view cycle is divided into four sub cycles a, b, c, and d as shown in FIG. 5. The number of sub cycles may be more than that of the combinations of the X-ray tube and the X-ray detector, for example.

Figure 6:
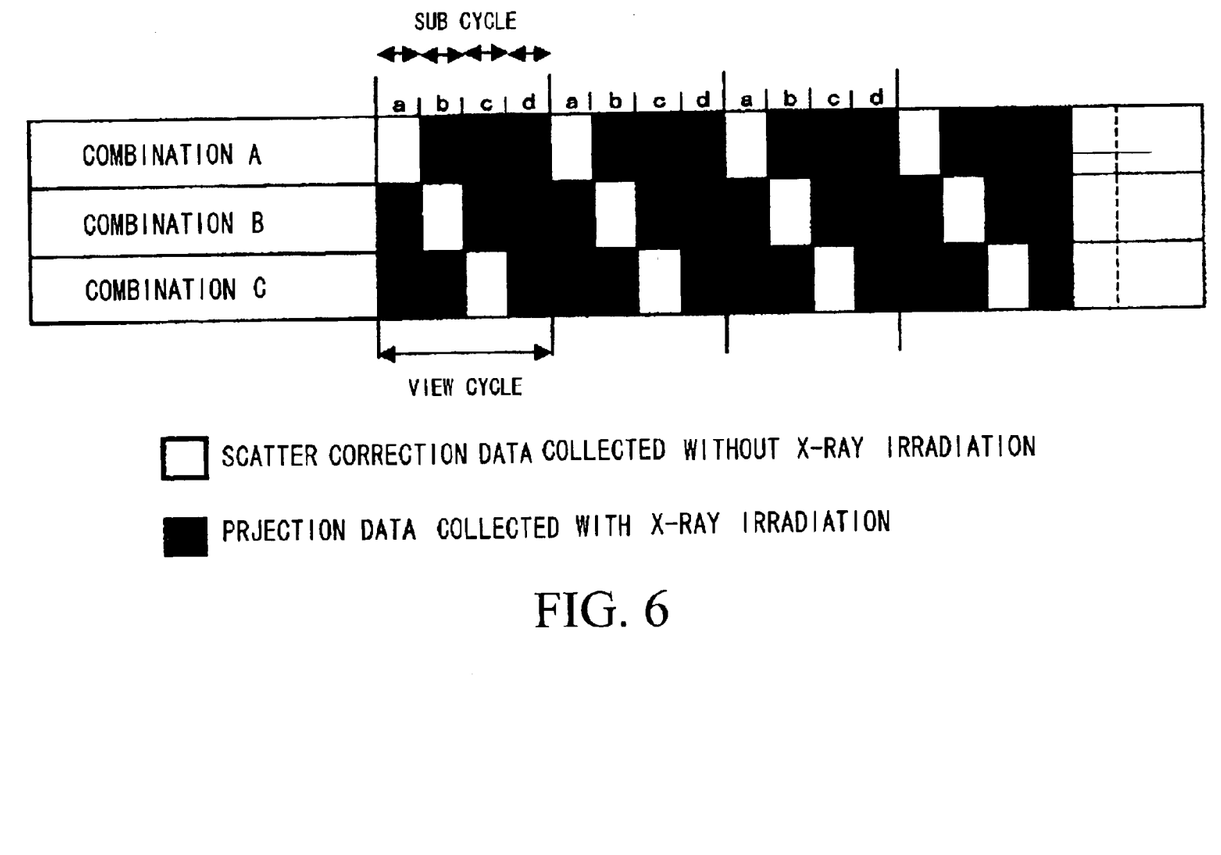
FIG. 6 is a more detailed illustration for explaining data collection timing by the X-ray CT apparatus in the first embodiment.

Data collection timing of each combination of the X-ray tube and the X-ray detector in the sub cycles a, b, c, and d is shown in FIG. 6. The projection data of 900 views×3 sub cycles and the scatter correction data of 900 views×1 sub cycle are collected in one view cycle. In FIG. 6, black portions indicate times when the projection data is collected and white portions indicate times when the scatter correction data is collected.

Figure 7:
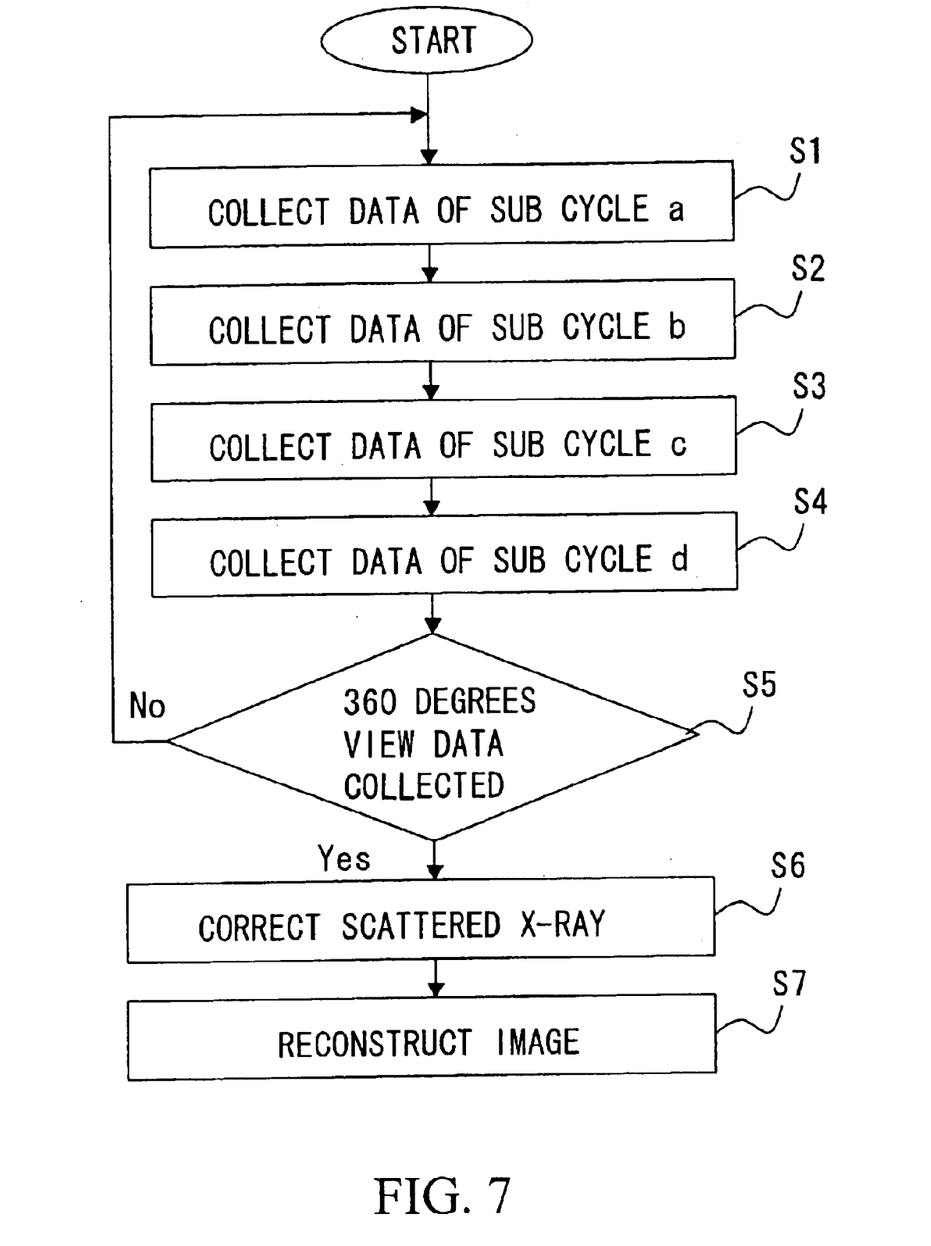
FIG. 7 is a flow chart of operation of data collection in the first embodiment.

More details are explained with reference to FIG. 7. In the sub cycle a, while the X-ray tube 1A of the combination A does not irradiate an X-ray and the X-ray tubes 1B and 1C irradiate X-rays, the detectors 6A, 6B, and 6C detect the X-ray (Step S1). In the sub cycle b, while the X-ray tube 1B of the combination B does not irradiate an X-ray and the X-ray tubes 1A and 1C irradiate X-rays, the all detectors 6A, 6B, and 6C detect the X-rays (Step S2). In the sub cycle c, while the X-ray tube 1C of the combination C does not irradiate an X-ray and the X-ray tubes 1A and 1B irradiate X-rays, the all detectors 6A, 6B, and 6C detect the X-ray (Step S3). In the sub cycle d, while the X-ray tubes 1A, 1B, and 1C of the combinations A, B, and C irradiate X-rays, all detectors 6A, 6B, and 6C detect the X-rays (Step S4).

The above mentioned operation is performed in the next view cycle when the X-ray tube 1A is positioned at 0 degrees (therefore, the X-ray tube B and the X-ray tube C are positioned at 120 degrees and 240 degrees). Thereafter, the operation is also performed in a subsequent view cycle when the X-ray tube 1A is positioned at 0.4 degrees (therefore, the X-ray tube B and the X-ray tube C are positioned at 120.4 degrees and 240.4 degrees, respectively). Moreover, the operation is also performed in the view cycle when the X-ray tube 1A is positioned at 0.8 degrees. The operation is repeatedly performed in all view cycles (Step S5).

Regarding the combination A, in the sub cycle a, the data detected by the detector 6A with irradiation from the X-ray tubes 1B and 1C and without irradiation from the X-ray tube 1A shows the scattered X-ray that scatters in the patient 4 based on the X-rays irradiated from the X-ray tubes 1B and 1C. Thus, the detected data is used as the scatter correction data. On the other hand, in the sub cycles b, c, and d, the X-ray detector 6A mainly detects the X-ray from the X-ray tube 1A penetrated through the patient 4 as the projection data.

Regarding the combination B, in the sub cycle b, when the X-ray tube 1B stops X-ray irradiation and the X-ray tubes 1A and 1C irradiate the X-rays, the X-ray detectors 6A, 6B, and 6C detect the X-rays. In this case, the data detected by the X-ray detector 6B shows scattered X-ray that is scattered in the patient 4 based on the X-rays irradiated from the X-ray tubes 1A and 1C. Thus, the detected data is used as the scatter correction data.

In the sub cycles a, c, and d, the X-ray detector 6B mainly detects the X-ray from the X-ray tube 1B penetrated through the patient 4 as the projection data. Similarly, regarding the combination C, in the sub cycle c, when the X-ray tube 1C stops X-ray irradiation and the X-ray tubes 1A and 1B irradiate the X-rays, the X-ray detectors 6A, 6B, and 6C detect the X-rays. In this case, the data detected by the X-ray detector 6C shows scattered X-ray scattering in the patient 4 based on the X-rays irradiated from the X-ray tubes 1A and 1B. Thus, the detected data is used as the scatter correction data. In the sub cycles a, b, and d, the X-ray detector 6C mainly detects the X-ray from the X-ray tube 1C penetrated through the patient 4 as the projection data. The above-mentioned projection data contains scattered X-ray data based on the X-ray irradiated from the X-ray tubes of the other combinations. Then, the projection data is corrected based on the scatter correction data to create the view data for the reconstruction.

More detailed explanation about the scatter correction is described below, taking the combination A as one example. In sub cycle a, data A' obtained by one channel of the detector 6A is $\beta(a)+\gamma(a)$. The $\beta$ is the scattered X-ray data based on the X-ray irradiated from the X-ray tube 1B and the $\gamma$ is scattered X-ray data based on the X-ray irradiated from the X-ray tube 1C. In the sub cycle b, data B' obtained by the channel of the detector 6A is $\alpha(b)+\gamma(b)$. The $\alpha$ is the projection data based on the X-ray irradiated from the X-ray tube 1A and penetrated through the patient 4. Data C' obtained in the sub cycle c is $\alpha(c)+\beta(c)$, and Data D' obtained in the sub cycle d is $\alpha(d)+\beta(d)+\gamma(d)$. Since time interval of sub cycles is short, the following formula can be theoretically assumed.

$$\alpha(a) \approx \alpha(b) \approx \alpha(c) \approx \alpha(d)$$

$$\beta(a) \approx \beta(b) \approx \beta(c) \approx \beta(d)$$

$$\gamma(a) \approx \gamma(b) \approx \gamma(c) \approx \gamma(d)$$

When the above values are assumed as $\alpha$, $\beta$ and $\gamma$, the following equation is established.

$$A' = \beta + \gamma$$

$$B' = \alpha + \gamma$$

$$C' = \alpha + \beta$$

$$D' = \alpha + \beta + \gamma$$

The scatter correction unit 22 calculates the following equation in all channels (Step S6).

$$3\alpha = B' + C' + D' - 2A'$$

The calculated value 3α is fed to the reconstruction unit 23 as the view data obtained in this view cycle. After the operation is repeatedly performed over 360 degrees (each detector rotates 120 degrees), the reconstruction unit 23 reconstructs the image based on the view data of 360 degrees and 900 views (Step S7). The reconstructed image is displayed on the display 24.

In the first non-limiting embodiment, since the projection data is corrected based on the scatter correction data and the image is reconstructed based on the corrected data, the quality of image and diagnosis accuracy improve. In addition, in the first embodiment, since the projection data and the scatter correction data are obtained in the short interval, the quality of the image greatly improves.

Figure 8:
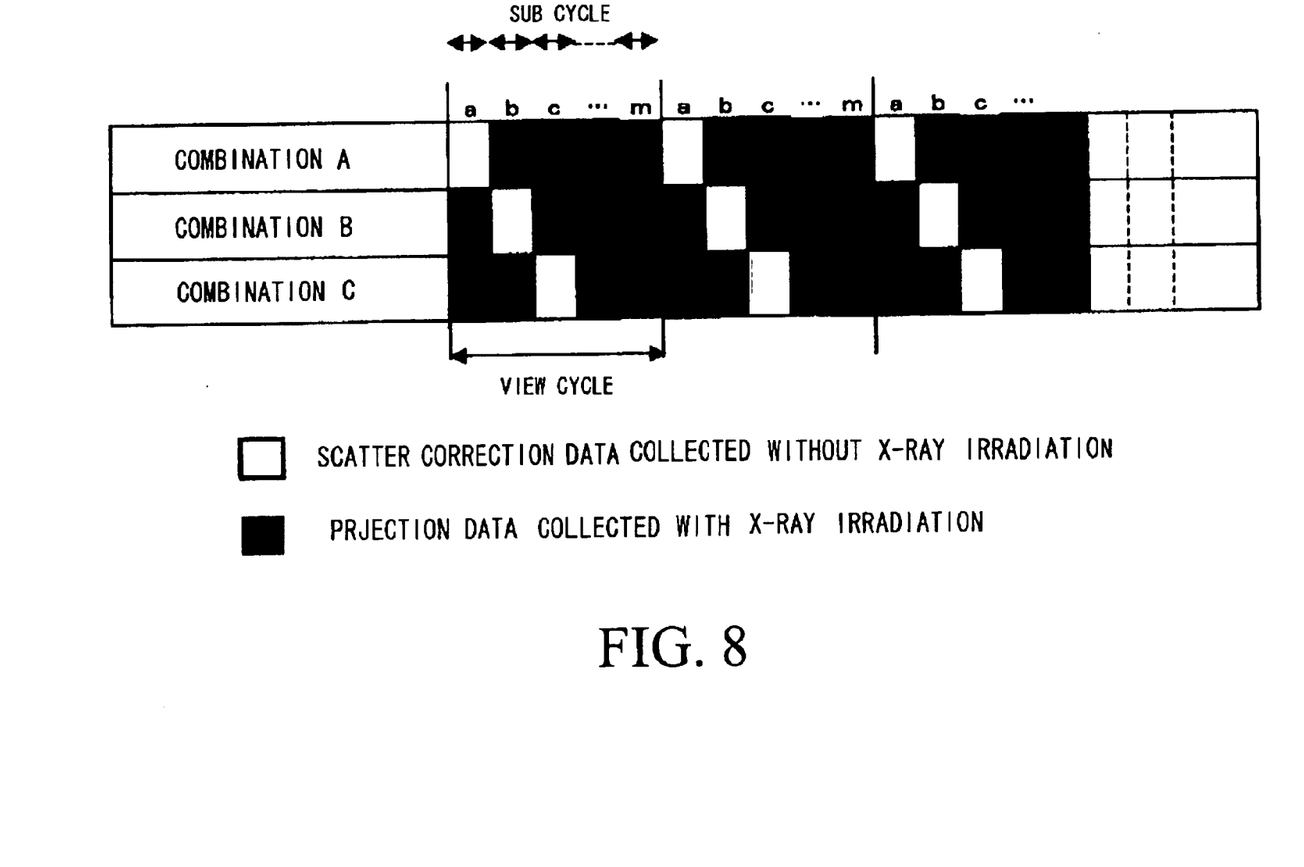
FIG. 8 is a detailed illustration for explaining data collection timing in a non-limiting alternative embodiment.

As a first non-limiting modification of the first embodiment, the number of sub cycles may be increased to positive integer "m," having a value more than four, as shown in FIG. 8. The scatter correction data may be obtained in one sub cycle, and the projection data may be obtained in m−1 sub cycles. In the first modification, since the time for collecting the scatter correction data is short and the time for collecting the projection data is long, it is possible to reduce deterioration of the quality of the image that results from a decrease in the amount of X-rays.

As a further modification, the amount of the X-ray may be increased according to the stop time of the X-ray irradiation. In the above case, the X-ray may be increased by m/(m−1) times. In comparison with a case where the X-ray is continuously irradiated, the image in which the scattered X-ray is reduced can be obtained with a similar amount of the X-ray.

Figure 9:
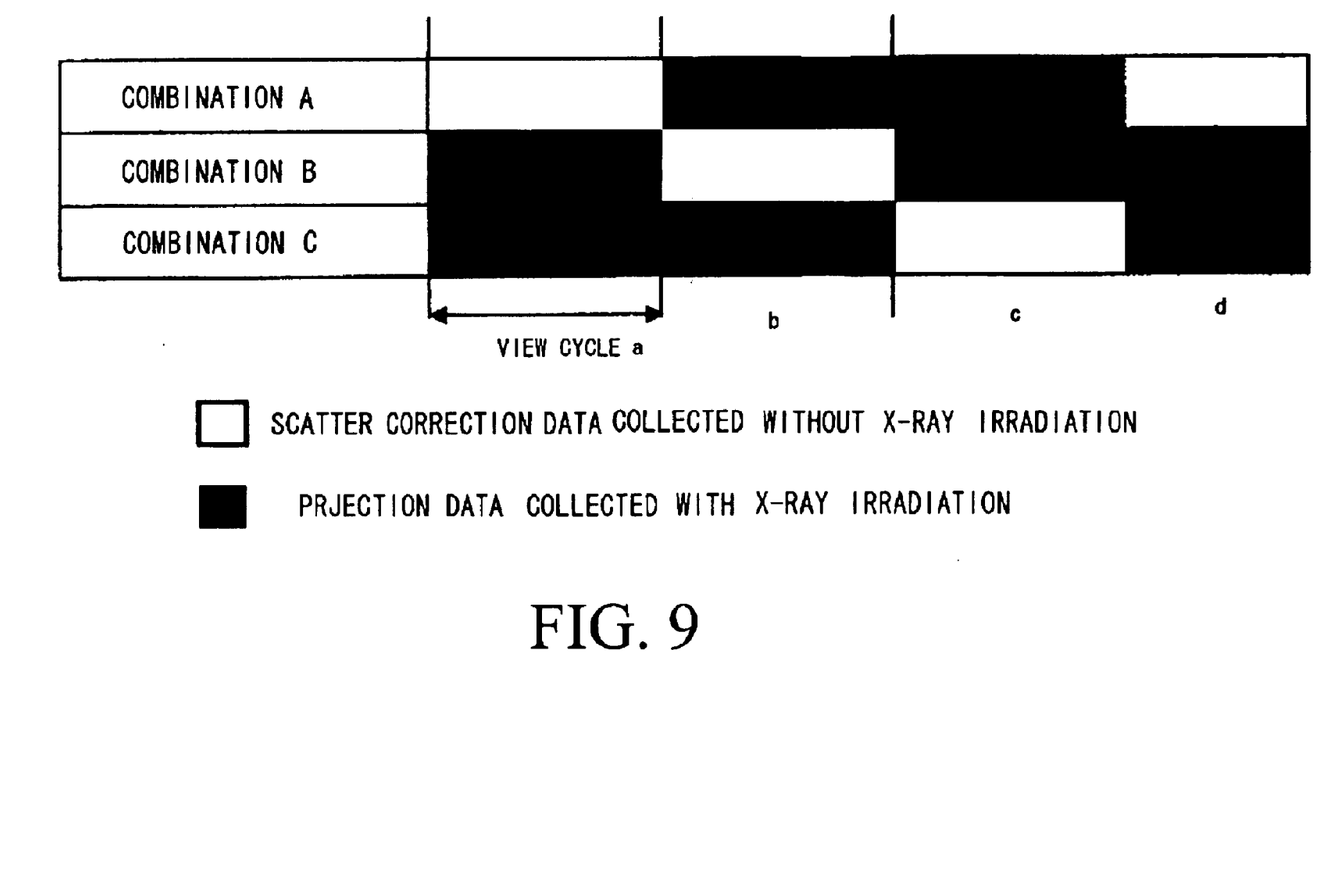
FIG. 9 is a detailed illustration for explaining data collection timing in another non-limiting alternative embodiment.

As a second non-limiting modification of the first embodiment, the number of the sub cycles may be three. In this case, the scatter correction data is obtained in one sub cycle a and the projection data is obtained in two sub cycles b and c. Data A', B' and C' obtained in the sub cycles a, b, and c are described by the following equations:

$$A' = \beta + \gamma$$

$$B' = \alpha + \gamma$$

$$C' = \alpha + \beta$$

The following equation is calculated to obtain the view data:

$$2\alpha = B' + C' - A'$$

The image is reconstructed based on the view data. In the second modification, the number of sub cycles may be equal to the number of the combinations of the X-ray tube and the X-ray detector.

As a third modification of the first embodiment, the view cycle is not divided into sub cycles, but the scatter correction data is collected by predetermined view cycles. For example, the scatter correction data is collected by three view cycles. Regarding combination A, in view cycles a and b, projection data A" and B" is collected. In a view cycle c, scatter correction data C" is collected. As described in the first embodiment, the α is the projection data based on the X-ray irradiated from the X-ray tube 1A and penetrated through the patient 4, the β is the scattered X-ray data based on the X-ray irradiated from the X-ray tube 1B, and the γ is scattered X-ray data based on the X-ray irradiated from the X-ray tube 1C. The following equations are established:

$$A'' = \beta + \gamma$$

$$B'' = \alpha + \gamma$$

$$C'' = \alpha + \beta$$

The view data in the view cycle b is calculated by the following equation:

$$2\alpha = A'' + B'' - C''$$

Also, the view data in the view cycle c is calculated by the following equation using projection data D" obtained in a view cycle d:

$$2\alpha = B'' + D'' - C''$$

The reconstruction unit 23 reconstructs the image based on the view data obtained by each view cycle. In the third non-limiting modification, since the data is not collected by a sub cycle but collected by a view cycle, sampling speed can be reduced in a theoretical sense.

The present invention may be not limited to the above embodiments, and various modifications may be made without departing from the spirit or scope of the general inventive concept. For example, an X-ray CT apparatus that includes a ring-shaped X-ray detector positioned on a face perpendicular to a rotation center of an X-ray tube, instead of the individual X-ray detector corresponding to the X-ray tube, may be applied.

Moreover, an X-ray CT apparatus that includes a multi slice X-ray detector having a plurality of detection elements lines arranged in a slice direction may be applied. Each detection elements line includes a plurality of detection elements arranged in a channel direction.

Furthermore, a helical X-ray CT apparatus where data is collected during X-ray tube rotating and a gantry or a bed moving, may be applied. Otherwise, a dynamic scanning X-ray CT apparatus that repeatedly obtains the same area image by keeping a patient at the same position and by scanning the same circular orbit may be used. Further, a half scan which reconstructs an image based on projection data of 180 degrees+fan angle degrees (the fan angle degrees being represented by Ω in FIG. 3, for example) may be applied.

Other calculation methods for the scatter correction may be used. Although the number of the combinations of the X-ray tube and the X-ray detector is three in the above embodiment, a greater or fewer number of combinations, such as two combinations, may be used. Although the number of views is described as 900 in the above embodiment, the number of views may be more or less than 900. Further, a Z-shifted X-ray CT apparatus where at least one X-ray tube is shifted to other X-ray tube in a slice direction, may be applied.

Numerous modifications and variations of the present invention are possible in light of the above teachings. It is therefore to be understood that within the scope of the appended claims, the invention may be practiced otherwise than as specifically described herein.

What is claimed is:

1. An X-ray CT apparatus, comprising:
   a plurality of X-ray irradiation sources configured to rotate around an object and to irradiate X-rays to the object;
   a plurality of X-ray detection units, each of which is positioned opposite each of the plurality of X-ray irradiation sources and configured to detect at least one X-ray penetrated through the object, thereby obtaining projection data and scatter correction data;

a control unit configured to divide a view cycle into a plurality of sub cycles, to allocate the plurality of sub cycles between obtaining the projection data and the scatter correction data, and to obtain view data by the view cycle based on the projection data and the scatter correction data; and a reconstruction unit configured to reconstruct an image of the object based on the view data.

2. The X-ray CT apparatus according to claim 1, wherein a number of the plurality of sub cycles is equal to a number of the plurality of X-ray irradiation sources.

3. The X-ray CT apparatus according to claim 1, wherein a number of the plurality of sub cycles is more than a number of the plurality of X-ray irradiation sources.

4. The X-ray CT apparatus according to claim 1, wherein a number of the plurality of sub cycles for obtaining the projection data is equal to a number of the plurality of sub cycles for obtaining the scatter correction data.

5. The X-ray CT apparatus according to claim 1, wherein a number of the plurality of sub cycles for obtaining the projection data is more than a number of the plurality of sub cycles for obtaining the scatter correction data.

6. The X-ray CT apparatus according to claim 5, wherein:

the number of the sub cycles is equal to a positive integer m, the projection data is obtained in (m−1) sub cycles, and the scatter correction data is obtained in a remaining sub cycle.

7. The X-ray CT apparatus according to claim 1, wherein at least one of the X-ray detection units obtains the projection data when at least another of the X-ray detection units obtains the scatter correction data.

8. The X-ray CT apparatus according to claim 1, wherein the plurality of X-ray irradiation sources are positioned in a single circle.

9. The X-ray CT apparatus according to claim 1, wherein the plurality of X-ray irradiation sources move in a helical orbit around the object.

10. The X-ray CT apparatus according to claim 1, wherein the plurality of X-ray irradiation sources repeatedly move in a circular orbit about the object.

11. The X-ray CT apparatus according to claim 1, wherein an amount of X-ray used to obtain the projection data increases.

12. The X-ray CT apparatus according to claim 1, wherein the plurality of X-ray detection units are positioned to form a ring-shaped face.

13. The X-ray CT apparatus according to claim 1, wherein each of the X-ray detection units includes detection elements arranged 2-dimensionally in channel and slice directions.

14. The X-ray CT apparatus according to claim 1, wherein the reconstruction unit is configured to reconstruct the image of the object based on the view data of 180 degrees+fan angle degrees.

15. The X-ray CT apparatus according to claim 1, wherein the reconstruction unit is configured to reconstruct the image of the object based on the view data of 360 degrees.

16. The X-ray CT apparatus according to claim 1, wherein the plurality of X-ray irradiation sources include three X-ray tubes.

17. The X-ray CT apparatus according to claim 1, wherein the plurality X-ray irradiation sources include two X-ray tubes.

18. An X-ray CT apparatus, comprising:

a plurality of X-ray irradiation sources configured to rotate around an object and to irradiate X-rays to the object;

a plurality of X-ray detection units, each of which is positioned opposite each of the plurality of X-ray irradiation sources and configured to detect at least one X-ray penetrated through the object; and a control unit configured to control the plurality of X-ray irradiation sources and the plurality of X-ray detection units such that at least one of the plurality of X-ray detection units obtains projection data when at least another of the plurality of X-ray detection units obtains scatter correction data.

19. An X-ray CT apparatus, comprising:

a plurality of X-ray tubes configured to rotate around an object and to irradiate X-rays to the object;

a plurality of X-ray detection units, each of which is positioned opposite to each of the plurality of X-ray tubes and is configured to detect at least one X-ray penetrated through the object; and a control unit configured to control the plurality of X-ray tubes and the plurality of X-ray detection units such that at least one of the plurality of X-ray detection units obtains projection data when at least another of the plurality of X-ray detection units obtains scatter correction data.

20. An X-ray CT apparatus, comprising:

a plurality of X-ray irradiation sources configured to rotate around an object and to irradiate X-rays to the object;

a plurality of X-ray detection units, each of which is positioned opposite to each of the plurality of X-ray irradiation sources and is configured to detect at least one X-ray penetrated through the object to obtain projection data and scatter correction data;

a control unit configured to obtain view data by a view cycle, based on the projection data and the scatter correction data; and a reconstruction unit configured to reconstruct an image of the object based on the view data.

21. An X-ray CT apparatus, comprising:

a plurality of irradiating means, rotating around an object, for irradiating X-rays to the object;

a plurality of detecting means, each of which is positioned opposite to the plurality of irradiating means, for detecting at least one X-ray penetrated through the object to obtain projection data and scatter correction data;

means for dividing a view cycle into a plurality of sub cycles, for allocating the sub cycle between obtaining the projection data and the scatter correction data, and for obtaining view data by the view cycle, based on the projection data and the scatter correction data; and means for reconstructing an image of the object based on the view data.

* * * * *